United States Patent
Lee

(10) Patent No.: US 8,410,301 B2
(45) Date of Patent: Apr. 2, 2013

(54) METHODS FOR THE SYNTHESIS OF ORGANIC SULFIDES BY USING SULFIDES AND ORGANIC SULFUR-INDIUM COMPLEXES

(75) Inventor: Phil-ho Lee, Chuncheon-si (KR)

(73) Assignee: Knu-Industry Cooperation Foundation (KR)

( * ) Notice: Subject to any disclaimer, the term of this patent is extended or adjusted under 35 U.S.C. 154(b) by 341 days.

(21) Appl. No.: 12/680,852

(22) PCT Filed: Oct. 10, 2008

(86) PCT No.: PCT/KR2008/005954
§ 371 (c)(1),
(2), (4) Date: Mar. 30, 2010

(87) PCT Pub. No.: WO2009/069888
PCT Pub. Date: Jun. 4, 2009

(65) Prior Publication Data
US 2010/0234633 A1    Sep. 16, 2010

(30) Foreign Application Priority Data
Nov. 28, 2007 (KR) .................. 10-2007-0122293

(51) Int. Cl.
*C07C 321/00* (2006.01)
*C07C 323/00* (2006.01)
*C07C 381/00* (2006.01)

(52) U.S. Cl. ........................................ 560/18

(58) Field of Classification Search ................ None
See application file for complete search history.

(56) References Cited

PUBLICATIONS

Nan Zheng et al., "Palladium-Catalyzed Synthesis of Aryl Sulfides from Aryl Triflates", The Journal of Organic Chemistry, 1998, vol. 63, No. 26, pp. 9606-9607.
Ignacio Perez et al., "Atom-Efficient Metal-Catalyzed Cross-Coupling Reaction of Indium Organometallics with Organic Electrophiles", Journal of the Amerian Chemical Society, 2001, vol. 123, No. 18, , pp. 4155-4160.
Ulrich Schopfer et al., "A general Palladium-Catalyzed Synthesis of Aromatic and Heteroaromatic Thioethers", Tetrahedron, 2001, vol. 57, pp. 3069-3073.
Phil Ho Lee et al., "Pd-Catalyzed Carbonylative Cross-Coupling Reactions by Triorganoindiums: Highly Efficient Transfer of Organic Groups Attached to Indium under Atmospheric Pressure", Organic Letters, 2003, vol. 5, No. 7, pp. 1103-1106.

International Search Report—PCT/KR2008/005954 dated Apr. 27, 2009.
Written Opinion—PCT/KR2008/005954.
Guang-Yao Gao, et al., Synthesis of meso-Arylsulfanyl- and alkylsulfanyl-Substituted Porphyrins via Palladium-Mediated C-S Bond Formation, J. Org. Chem., vol. 69, No. 25, 2004, pp. 8886-8892.
Takahiro Itoh, et al., A General Palladium-Catalyzed Coupling of Aryl Bromides/Triflates and Thiols, Organic Letters, vol. 6, No. 24, 2004, pp. 4587-4590.
Miki Murata, et al., A General and Efficient Method for the Palladium-Catalyzed Cross-Coupling of Thiols and Secondary Phosphines, Tetrahedron, vol. 60, 2004, pp. 7397-7403.
Clotilde Mispelaere-Canivet, et al., Pd2(dba)3/Xantphos-catalyzed cross-coupling of thiols and aryl bromides/triflates, Tetrahedron, vol. 61, 2005, pp. 5253-5259.
Christian Wol,F et al., Use of Highly Active Palladium-Phosphinous Acid Catalysts in Stille, Heck, Amination, and Thiation Reactions of Chloroquinolines, J. Org. Chem., vol. 68, No. 18, 2003, pp. 7077-7084.
Craig G. Bates, et al., Copper-Catalyzed Synthesis of Vinyl Sulfides, Organic Letters, vol. 6, No. 26, 2004, pp. 5005-5008.
Cecile Savarin, et al., A Mild, Nonbasic Synthesis of Thioethers. The Copper-Catalyzed Coupling of Boronic Acids with N-Thio(alkyl, aryl, heteroary)imides, Organic Letters, vol. 4, No. 16, 2002, pp. 4309-4312.
Craig G. Bates, et al., A General Method for the Formation of Aryl-Sulfur Bonds Using Copper(I) Catalysts, Organic Letters, vol. 4, No. 16, 2002, pp. 2803-2806.
Monica Carril, et al., Simple and Efficient Recyclable Catalytic System for Performing Copper-Catalysed S-Arylation Reactions in the Presence of Water, Chem. Eur. J., 13, 2007, pp. 5100-5105.
Ying-Chieh Wong, et al., Colbalt-Catalyzed Aryl-Sulfur Bond Formation, Organic Letters, vol. 8, No. 24, 2006, pp. 5613-5616.
Manuel A. Fernandez-Rodriguez, et al., A General and Long-Lived Catalyst for the Palladium-Catalyzed Coupling of Aryl Halides with Thiols, J. Am. Chem. Soc., vol. 128, No. 7, 2006, pp. 2180-2181.
Yugen Zhang, et al., The First N-Heterocyclic Carbene-Based Nickel Catalyst for C-S Coupling, Organic Letters, vol. 9, No. 18, 2007, pp. 3495-3498.
Yao-Jung Chen, et al., 1,1,1-Tris(hydroxymethyl)ethane as a New, Efficient, and Versatile Tripod Ligand for Copper-Catalyzed Cross-Coupling Reactions of Aryl Iodidies with Amides, Thiols, and Phenols, Organic Letters, 2006, vol. 8, No. 24, pp. 5609-5612.

*Primary Examiner* — Johann R Richter
*Assistant Examiner* — Jennifer C Sawyer
(74) *Attorney, Agent, or Firm* — Cantor Colburn LLP

(57) ABSTRACT

The present invention relates to a novel synthesis method for the formation of carbon-sulfur bonds by the reaction of an organic sulfur-indium complex with nucleophile in the presence of a palladium catalyst. The present invention provides a synthesis method to prepare several kinds of organic sulfides which are difficult to be prepared by the conventional synthesis methods. A short reaction time and quantitative yield are the advantages of this method. In addition, several kinds of organic sulfide can be prepared by the selection of nucleophile and organic sulfur-indium complex to be used.

9 Claims, No Drawings

METHODS FOR THE SYNTHESIS OF ORGANIC SULFIDES BY USING SULFIDES AND ORGANIC SULFUR-INDIUM COMPLEXES

BACKGROUND OF THE INVENTION

1. Field of the Invention

The present invention relates to a method for the synthesis of an organic sulfide by the reaction of a sulfide with an organic sulfur-indium complex. More specifically, the conventional synthesis method for the formation of carbon sulfur bonds is carried out by the reaction between a nucleophile and an electrophile in the presence of a transition metal catalyst. An organic halide compound is used as an electrophile and a thiol is used as a nucleophile. A thiolate ion instead of a thiol is used as a nucleophile because a thiolate ion has more nucleophilicity than a thiol. And this conventional synthesis method requires high temperature and long reaction time. Therefore, an object of this invention is to provide a new type of reagent for the increase of nucleophilicity of a thiol and a high yield of organic sulfide in a relatively short reaction time. The synthesis methods of this invention are useful for the preparation of an organic sulfide whose synthesis method is not reported so far and which is difficult to be prepared. Another object of the present invention is to provide an effective and new synthesis method which can be carried out without an excess amount of reagents. The yield is quantitative when a nucleophile containing two or more nucleophilic sites in the compound is used.

2. Description of the Related Art

The conventional carbon-sulfur bonds formation reaction between an aromatic halide and a thiol in the presence of transition metal catalyst is carried out by the use of an atmospherically unstable strong base instead of a general base. This reaction requires long reaction time and high temperature. It is reported that a transition metal catalyst such as, Cu, Co, Ni, or Pd is used for the reaction. However, an excess amount of reagents, expensive ligands and additives are required for the formation of carbon-sulfur bonds in the conventional method. Therefore, the carbon-sulfur bond formation is difficult under mild reaction conditions and also it is difficult to control the regioselectivity of the reaction depending on the functional group of the substrate when a transition metal catalyst is not used in the reaction.

The formation of carbon-sulfur bonds by the reaction of aromatic triflate with a thiol in the presence of sodium t-butoxide and a palladium catalyst is reported (N. Zheng, et al., J. Org. Chem., 63, 9606 (1998)). However, the usefulness of this method has a limit and heating is required for 24 hours.

The formation of carbon-sulfur bonds by the reaction of aromatic iodide with a thiol in the presence of potassium t-butoxide and a palladium catalyst is reported (A. Schlapbach, et al., Tetrahedron, 57, 3069 (2001)). The reaction is limited to an aromatic iodide and potassium t-butoxide is necessarily required.

The formation of carbon-sulfur bonds by the reaction of aromatic boronic acid with a thio imide in the presence of a copper catalyst is reported (L. S. Leibeskind et al., Org. Lett., 4, 4309 (2002)). 24 hours of reaction time is required.

The formation of carbon-sulfur bonds by the reaction of aromatic iodide with a thiol in the presence of sodium t-butoxide and a copper neocuprine catalyst is reported (D. Venkataraman, et al., Org. Lett., 4, 2803 (2002)). However, the usefulness of this method is limited to aromatic iodide and the reaction is carried out for 24 hours at 110 degrees Celsius.

The formation of carbon-sulfur bonds by the reaction of aromatic halide with a thiol in the presence of a palladium catalyst and various kinds of base is reported (R. Lerebours, et al., J. Org. Chem., 68, 7077 (2003)). The reaction is carried out for 48 hours in toluene at high temperature.

The formation of carbon-sulfur bonds by the reaction of unsaturated iodide with a thiol in the presence of a copper-neocuprine catalyst and $K_3PO_4$ is reported (D. Venkataraman, et al., Org. Lett., 6, 5005 (2004)). However, the usefulness of this method is limited to unsaturated iodide and the reaction is carried out at 110 degrees Celsius.

The formation of carbon-sulfur bonds by the reaction of aromatic halide with a thiol in the presence of a palladium catalyst and $Cs_2CO_3$ is reported (P. Zhang et al., J. Org. Chem., 69, 8886 (2004)). This reaction requires an excess amount of reagents and over 20 hours of heating.

The formation of carbon-sulfur bonds by the reaction of aromatic halide with a thiol in the presence of a palladium catalyst and i-$Pr_2$NEt base is reported (T. Itoh et al., Org. Lett., 6, 4587 (2004)). This reaction requires an excess amount of catalyst and long reaction time The formation of carbon-sulfur bonds by the reaction of aromatic halide with a thiol in the presence of palladium catalyst and sodium t-butoxide is reported (S. L. Buchwald, et al., Tetrahedron, 60, 7397 (2004)). This reaction requires a strong base and is carried out for 18 hours in dioxane.

The formation of carbon-sulfur bonds by the reaction of aromatic halide with a thiol in the presence of palladium catalyst and $K_2CO_3$ is reported (P. Belslin, et al., Tetrahedron, 61, 5253 (2005)). This reaction is carried out for 24 hours at 140 degrees Celsius in xylene.

The formation of carbon-sulfur bonds by the reaction of unsaturated halide with a thiol in the presence of a copper diammine catalyst is reported (I. Tellitu, et al., Chem. Eur. J., 13, 5100 (2006)). This reaction requires two times usage of reagents and is carried out for 10 hours at 120 degrees Celsius.

The formation of carbon-sulfur bonds by the reaction of aromatic iodide with a thiol in the presence of a copper-tripod catalyst and $Cs_2CO_3$ is reported (Y. J. Chen, et al., Org. Lett., 8, 5609 (2006)). Aromatic iodide is the only used halide and the reaction is carried out for 24 hours of heating.

The formation of carbon-sulfur bonds by the reaction of aromatic halide with a thiol in the presence of a cobalt-zinc catalyst and pyridine is reported (C. H. Cheng, et al., Org. Lett., 8, 5613 (2006). More than one equivalent of zinc is used as a reducing agent and the reaction is carried out for 10 hours of heating.

The formation of carbon-sulfur bonds by the reaction of aromatic halide with a thiol in the presence of a palladium catalyst is reported (J. F. Hartwig, et al., J. Am. Chem. Soc., 128, 2180, (2006)). The ligand is specially designed for this reaction and the reaction should be carried out under strong basic conditions at high temperature.

The formation of carbon-sulfur bonds by the reaction of aromatic halide with a thiol in the presence of a Ni—NHC catalyst and potassium t-butoxide is reported (J. Y. Ying, et al., Org. Lett., 9, 3495 (2007)). This reaction requires a strong base and 16 hours of heating.

The formation of carbon-sulfur bonds by the reaction of aromatic iodide with a thiol in the presence of a copper diammine catalyst is reported (E. Dominguez, et al., Chem. Eur. J., 13, 5100 (2007)). Aromatic iodide is the only used halide and this reaction is carried out for more than 10 hours at 120 degrees Celsius in water.

SUMMARY OF THE INVENTION

The present invention relates to a method for the synthesis of an organic sulfide by the reaction of a sulfide with an organic sulfur-indium complex. More specifically, the conventional synthesis method for the formation of carbon sulfur bonds is carried out by the reaction between a nucleophile and an electrophile in the presence of a transition metal catalyst. An organic halide compound is used as an electrophile and a thiol is used as a nucleophile. A thiolate ion instead of thiol is used as nucleophile because a thiolate ion has more nucleophilicity than a thiol. And this conventional synthesis method requires high temperature and long reaction time. Therefore, an object of this invention is to provide a new type of reagent for the increase of nucleophilicity of a thiol and a high yield of organic sulfide in a relatively short reaction time. The synthesis methods of this invention are useful for the preparation of an organic sulfide whose synthesis method is not reported so far and which is difficult to be prepared. Another object of this invention is to provide an effective and new synthesis method which can be carried out without an excess amount of reagents. The yield is quantitative when a nucleophile containing two or more nucleophilic sites in the compound is used.

DETAILED DESCRIPTION OF THE PREFERRED EMBODIMENTS

Hereinafter, synthesis methods for the preparation of organic sulfides by the use of organic sulfur-indium complexes in accordance with the present invention will be described in more detail.

The present invention provides synthesis methods of organic sulfides by the use of following reagents represented in formula 1, 2, 3, and 4.

$R^1(SR)_n$ [formula 1]

$In(SR)_3$ [formula 2]

$R^1—X_m$ [formula 3]

[formula 4]

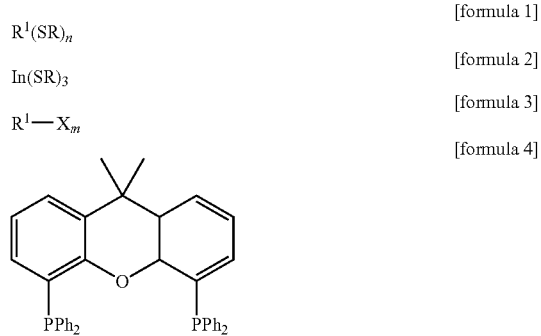

$R^1$ of organic sulfide (formula 1) represents a phenyl; an aromatic having linear or branched alkyl groups of 1 to 6 carbon atoms; an aromatic having linear or branched alkoxy groups of 1 to 6 carbon atoms; an aromatic having a halide, ester, nitro, aldehyde, ketone, cyanide, amide, or carboxylic acid group; or a linear or branched alkyl group of 1 to 6 carbon atoms attached to sp or $sp^2$ hybridized carbon. Furthermore, the present invention can be applied to the compound $R^1—X_m$ (formula 3) having a structure capable of the formation of two or more carbon-sulfur bondss.

R of organic sulfide (formula 1) represents a phenyl; an aromatic having linear or branched alkyl groups of 1 to 6 carbon atoms; an aromatic having linear or branched alkoxy groups of 1 to 6 carbon atoms; an aromatic having a halide, ester, nitro, aldehyde, ketone, cyanide, amide, or carboxylic acid group; a heterocyclic aromatic containing nitrogen, oxygen or sulfur; or a linear or branched alkyl of 1 to 6 carbon atoms.

In more detail, the organic sulfide (formula 1) can be prepared by the cross-coupling reaction between the organic sulfur-indium complex (formula 2) and nucleophile (formula 3) in the presence of a palladium-Xantphos catalyst.

The phosphine ligand in the present invention is selected from the group consisting of Xantphos, DPEphos (Bis(2-diphenylphosphinophenyl)ether), (Biph)PCy$_2$ (Cy=Cyclohexyl), DPPF (1,1'-Bis(diphenylphosphino)ferrocene), DPPE (1,2-Bis(diphenylphosphino)ethane), DPPP (1,3-Bis(diphenylphosphino)propane), Imes (1,3-Bis-di-i-propylphenyl)imidazolium chloride). Xantphos (formula 4) is the best ligand among the above ligands for the activation of palladium.

Nucleophiles used in this invention are aromatic halide, aromatic pseudo halide, unsaturated halide and unsaturated pseudo halide. The functional group in the aromatic compound and the pseudo halide do not have a significant effect on this reaction.

The halide X in formula 3 is Cl, Br, or I. The pseudo halide in formula 3 is triflate, ($—OSO_2CF_3$), methanesulfonate ($—OSO_2CH_3$), toluenesulfonate ($—OC_4H_6CH_3$), iodonium [$RI^+PhBF_4^-$, $RI^+Br^-$, R=Ph, 2-thienyl, 4-methoxyphenyl, trans-β-styryl] or azonium salt ($-N_2^+X^-$, X=Cl, Br, I).

R (formula 1) derived from organic sulfur-indium complex (formula 2) is a phenyl, p-tryl, p-anisyl, p—F—$C_6H_4$, t-butyl, i-propyl or n-propyl. And other groups can be used. The structure of a product can be determined by the control of functional group R in the indium complex (formula 2).

The used amount of the organic sulfur indium complex according to this invention is n/3 (n=1, 2, 3, 4) times an equivalent weight of the nucleophile depending on the number (m=1, 2, 3, 4) of halide or pseudo halide represented as X in Formula 3.

The catalyst used in the present invention is a palladium catalyst which is selected from the group consisting of $PdCl_2$, $PdBr_2$, $Pd(OAc)_2$, $Pd(CH_3CN)_2Cl_2$, $Pd(PhCN)_2Cl_2$, $Pd_2dba_3CHCl_3$, $Pd(PPh_3)_4$, and $[(allyl)PdCl]_2$. The additive is selected from the group consisting of LiCl, LiBr, LiI, $K_3PO_4$, $Na_2CO_3$, $Cs_2CO_3$, $Me_2NBu''$, pyridine, TEA (triethylamine), DIPEA (diisopropylethylamine), N-Methylpyrrolidione, and N-methylpiperidine. The used amount of the palladium catalyst and the additive are in the range of 1 to 10 mol % of a nucleophile.

The amount of a lithium halide (LiX; X=Cl, Br, I), an inorganic compound, an organic amine, or a base additive is in the range of 1.0 to 4.0 times an equivalent weight of the nucleophile. The solvent for the reaction is selected from the group consisting of dimethylformamide, dimethylacetamide, toluene, xylene and tetrahydrofuran. The reaction temperature is in the range of 70~110 degrees Celsius.

Xantphos is the most effective ligand in the present invention and the best result of carbon-sulfur coupling reaction can be obtained when the reaction is carried out in the presence of 4 mol % of Xantphos ligand for 2 to 4 hours at 100 degrees Celsius in DMF solvent. The yield is almost quantitative.

The synthesis method of the present invention can also be applied to prepare several kinds of organic sulfides (formula 1) by using various kinds of nucleophile (formula 3) and organic sulfur-indium complex (formula 2). For example, naphtyl, aromatic compounds having various kinds of functional group, hetero aromatic compounds having N, O or S, an unsaturated halide or an unsaturated pseudo halide can be used. Various kinds of organic group which can be derived from an organic sulfur-indium complex can be used. Therefore, several kinds of organic sulfide can be prepared according to the present invention by the combination of a nucleophile and an organic sulfur-indium complex.

EXAMPLES

Hereinafter, the present invention will be described in more detail with reference to the following Examples. These examples are provided only for illustrating the present invention and should not be construed as limiting the scope and spirit of the present invention.

Example 1

Preparation of 2-Phenylnaphthyl Sulfide

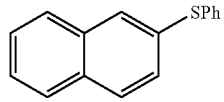

[formula 5]

A solution of palladium acetate (4.5 mg, 0.02 mmol) and Xantphos (12.7 mg, 0.022 mmol) in DMF (1 mL) was stirred for 5 minutes under a nitrogen atmosphere. To this solution was added 2-bromo naphthalene (103.5 mg, 0.5 mmol) dissolved in 0.5 mL of DMF and then the mixture was stirred for 10 minutes at room temperature. In(SPh)$_3$ (74 mg, 0.167 mmol) in DMF (1 mL) and diisopropylethyl amine (65 mg, 0.5 mmol) were added to this reaction mixture. The reaction mixture was stirred for 2 hours at 100 degrees Celsius. The solution was cooled to room temperature and then 1 mL of hydrochloric acid (5% of aqueous solution) was added to stop the reaction. The crude product was extracted with diethyl ether (15 mL, 3 times) and sequentially washed with 10 mL of water, a saturated NaHCO$_3$ (10 mL) solution and a saturated NaCl (20 mL) solution. The extracted organic compound was dried over anhydrous MgSO$_4$ and then filtered. After evaporation of the solvents, the crude product was purified by column chromatography to give 2-phenylnaphthyl sulfide (112 mg, 95%) (formula 5).

$^1$H-NMR (300 MHz, CDCl$_3$, 25 degrees Celsius) δ 7.8-8.74 (m, 4H), 7.49~7.36 (m, 5H), 7.33-7.23 (m, 3H).

Example 2

Preparation of Ethyl-3-Isopropylthiobenzoate

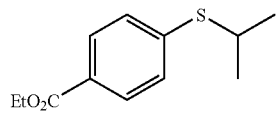

[formula 6]

A solution of palladium acetate (4.5 mg, 0.02 mmol) and Xantphos (12.7 mg, 0.022 mmol) in DMF (1 mL) was stirred for 5 minutes under a nitrogen atmosphere. To this solution was added ethyl 3-bromobenzoate (114.5 mg, 0.5 mmol) dissolved in 0.5 mL of DMF and then the reaction mixture was stirred for 10 minutes at room temperature. In(SPr')$_3$ (57 mg, 0.168 mmol) in DMF (1 mL) and diisopropylethyl amine (65 mg, 0.5 mmol) were added to this reaction mixture. The reaction mixture was stirred for 2 hours at 100 degrees Celsius. The solution was cooled to room temperature and then 1 mL of hydrochloric acid (5% of aqueous solution) was added to stop the reaction. The crude product was extracted with diethyl ether (15 mL, 3 times) and sequentially washed with 10 mL of water, a saturated NaHCO$_3$ (10 mL) solution and a saturated NaCl (20 mL) solution. The extracted organic compound was dried over anhydrous MgSO$_4$ and then filtered. After evaporation of solvents, the crude product was purified by column chromatography to give ethyl-3-isopropylthio benzoate (102 mg, 91%) (formula 6).

$^1$H-NMR (400 MHz, CDCl$_3$, 25 degrees Celsius) δ 8.06 (s, 1H), 7.89 (d, J=7.8 Hz, 1H), 7.56 (d, J=7.8 Hz, 1H), 7.36 (t, J=7.8 Hz, 1H), 4.38 (q, J=7.1 Hz, 2H), 3.44 (sep, J=6.7 Hz, 1H), 1.40 (t, J=7.1 Hz, 3H), 1.31 (d, J =6.7 Hz, 6H).

Example 3

Preparation of 1-Phenylnaphthylsulfide

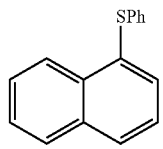

[formula 7]

A solution of palladium acetate (4.5 mg, 0.02 mmol) and Xantphos (12.7 mg, 0.022 mmol) in DMF (1 mL) was stirred for 5 minutes under a nitrogen atmosphere. To this solution was added 1-naphthyltrifluoromethanesulfonate (138.1 mg, 0.5 mmol) dissolved in 0.5 mL of DMF and then the reaction mixture was stirred for 10 minutes at room temperature. In(SPh)$_3$ (74 mg, 0.167 mmol) in DMF (1 mL) and diisopropylethyl amine (65 mg, 0.5 mmol) were added to this reaction mixture. The reaction mixture was maintained for 2 hours at 100 degrees Celsius. The solution was cooled to room temperature and then 1 mL of hydrochloric acid (5% of aqueous solution) was added to stop the reaction. The crude product was extracted with diethyl ether (15 mL, 3 times) and sequentially washed with 10 mL of water, a saturated NaHCO$_3$ (10 mL) solution and a saturated NaCl (20 mL) solution. The extracted organic compound was dried over anhydrous MgSO$_4$ and then filtered. After evaporation of solvents, the crude product was purified by column chromatography to give 1-phenylnaphthylsulfide (112 mg, 95%) (formula 7).

$^1$H-NMR (300 MHz, CDCl$_3$) δ 8.40-8.38 (m, 1H), 7.90~7.85 (m, 2H), 7.67 (d, J=7.21 Hz, 1H), 7.52-7.49 (m, 2H), 7.43 (t, J=8.4 Hz, 1H), 7.25~7.17 (m, 5H).

Example 4

Preparation of trans-β-styrenyl-phenylsulfide

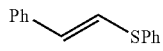

[formula 8]

A solution of palladium acetate (4.5 mg, 0.02 mmol) and Xantphos (12.7 mg, 0.022 mmol) in DMF (1 mL) was stirred for 5 minutes under a nitrogen atmosphere. To this solution was added 1-bromostyrene (91.5 mg, 0.5 mmol) dissolved in 0.5 mL of DMF and then the reaction mixture was stirred for 10 minutes at room temperature. In(SPh)$_3$ (74 mg, 0.167 mmol) in DMF (1 mL) and diisopropylethyl amine (65 mg, 0.5 mmol) were added to this reaction mixture. The reaction mixture was stirred for 2 hours at 100 degrees Celsius. The solution was cooled to room temperature and then 1 mL of hydrochloric acid (5% of aqueous solution) was added to stop the reaction. The crude product was extracted with diethyl ether (15 mL, 3 times) and sequentially washed with 10 mL of water, a saturated NaHCO$_3$ (10 mL) solution and a saturated NaCl (20 mL) solution. The extracted organic compound was dried over anhydrous MgSO$_4$ and then filtered. After evaporation of solvents, the crude product was purified by column chromatography to give trans-beta-styrenyl-phenylsulfide (101 mg, 95%) (formula 8).

$^1$H-NMR (300 MHz, CDCl$_3$) δ 7.60 (m, 10H), 6.70 (d, J=15.4 Hz, 1H), 6.62 (d, J=15.4 Hz, 1H).

Example 5

Preparation of Ethyl-2-phenylsulfynyl-cyclohex-1-ene carboxylate

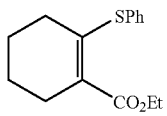

[formula 9]

A solution of palladium acetate (4.5 mg, 0.02 mmol) and Xantphos (12.7 mg, 0.022 mmol) in DMF (1 mL) was stirred for 5 minutes under a nitrogen atmosphere. To this solution was added ethyl-2-trifluoromethanesulfonyloxo benzoate (151.0 mg, 0.5 mmol) dissolved in 0.5 mL of DMF and then the reaction mixture was stirred for 10 minutes at room temperature. In(SPh)$_3$ (74 mg, 0.167 mmol) in DMF (1 mL) and diisopropylethyl amine (65 mg, 0.5 mmol) were added to this reaction mixture. The reaction mixture was stirred for 2 hours at 100 degrees Celsius. The solution was cooled to room temperature and then 1 mL of hydrochloric acid (5% of aqueous solution) was added to stop the reaction. The crude product was extracted with diethyl ether (15 mL, 3 times) and washed with 10 mL of water, saturated NaHCO$_3$ (10 mL) solution and saturated NaCl (20 mL). The extracted organic compound was dried over anhydrous MgSO$_4$ and then filtered. After evaporation of solvents, the crude product was purified by column chromatography to give ethyl 2-phenylsulfynyl-cyclohex-1-ene carboxylate (125 mg, 95%) (formula 9).

$^1$H-NMR (400 MHz, CDCl$_3$) δ 7.51-7.49 (m, 2H), 7.35-7.32 (m, 3H), 4.26 (q, J=7.2 Hz, 2H), 2.42-2.40 (m, 2H), 2.02-1.99 (m, 2H), 1.61-1.52 (m, 4H), 1.32 (t, J=7.2 Hz, 3H).

Example 6

Preparation of β,β-bis(isopropylthio)styrene

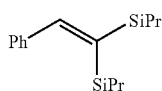

[formula 10]

A solution of palladium acetate (4.5 mg, 0.02 mmol) and Xantphos (12.7 mg, 0.022 mmol) in DMF (0.7 mL) was stirred for 5 minutes under a nitrogen atmosphere. To this solution was added β,β-dibromostyrene (105.0 mg, 0.4 mmol) dissolved in 0.4 mL of DMF and then the reaction mixture was stirred for 10 minutes at room temperature. In(SiPr)$_3$ (93 mg, 0.273 mmol) in DMF (0.8 mL) and diisopropylethyl amine (52 mg, 0.4 mmol) were added to this reaction mixture. The reaction mixture was stirred for 2 hours at 100 degrees Celsius. The solution was cooled to room temperature and then 1 mL of hydrochloric acid (5% of aqueous solution) was added to stop the reaction. The crude product was extracted with diethyl ether (15 mL, 3 times) and sequentially washed with 10 mL of water, a saturated NaHCO$_3$ (10 mL) solution and a saturated NaCl (20 mL) solution. The extracted organic compound was dried over anhydrous MgSO$_4$ and then filtered. After evaporation of solvents, the crude product was purified by column chromatography to give β,β-bis(isopropylthio)styrene (119 mg, 93%) (formula 10).

$^1$H-NMR (400 MHz, CDCl$_3$) δ 7.84 (d, J=7.6 Hz, 2H), 7.54 (dd, J=7.6, 6.7 Hz, 2H), 7.41 (d, J=6.7 Hz, 1H), 3.73 (sep, J=6.8 Hz, 1H), 3.62 (d, J=6.8 Hz, 1H), 1.52 (d, J=6.8 Hz, 6-H), 1.46 (d, J=6.8 Hz, 6H).

What is claimed is:
1. A method for the preparation of an organic sulfide compound of formula 1 comprising,
reacting a nucleophile of formula 3 and an organic sulfur-indium complex of formula 2 to form the organic sulfide compound of formula 1, wherein in formula 1 R$^1$ is derived from the nucleophile of formula 3 and R is derived from the organic sulfur-indium complex of formula 2,

R$^1$(SR)$_n$          formula 1

In(SR)$_3$          formula 2

R$^1$—X$_m$          formula 3 wherein
m is 1 or 2; when m is 1, R$^1$ is 1-naphthyl, 2-napthyhyl, 3-ethoxycargonylphenyl, 2-styryl, or ethoxycarbonyl-1-cyclohexane-2-yl, and n is 1; and when m is 2, R$^1$ is

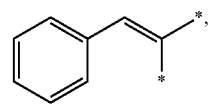

and n is 2;
R is a phenyl or a linear or branched alkyl group of 1 to 6 carbon atoms; and
X is Cl, Br, I, —OSO$_2$CF$_3$, —OSO$_3$CH$_3$, —OC$_4$H$_6$CH$_3$ iodonium of formula RI$^4$PhBF$_4^-$ or RI$^4$Br$^-$, wherein R is Ph, 2-thienyl, 4-methoxyphenyl, or trans-beta-styryl, or an azonium salt of formula —N$_2^+$X$^-$, wherein X is Cl, Br, or I.

2. The method according to claim 1, wherein the amount of the organic sulfur indium complex to be used is n/3 (n=1, 2) times an equivalent weight of the nucleophile depending on the number (m=1,2) of X in formula 3.

3. The method according to claim 1, wherein a palladium catalyst is used in the reaction and is selected from the group consisting of PdCl$_2$, PdBr$_2$, Pd(OAc)$_2$, Pd(CH$_3$CN)$_2$Cl$_2$, Pd(PhCN)$_2$Cl$_2$, Pd$_2$dba$_3$CHCl$_3$, Pd(Ph$_3$)$_4$ and [(allyl)PdCl]$_2$.

4. The method according to claim 1, wherein a phosphine ligand is used in the reaction and is selected from the group consisting of Xantphos, DPEphos (Bis(2-diphenylphosphinophenyl)ether), (Biph)PCy$_2$ (Cy=Cyclohexyl), DPPF (1,1'-Bis(diphenylphosphino)ferrocene), DPPE (1,2-Bis(diphenylphosphino)ethane), DPPP (1,3-Bis(diphenylphosphino)propane) and Imes (1,3-Bis-di-1-propylphenyl)imidazolium chloride).

5. The method according to claim 1, wherein the an additive is used in the reaction and is selected from the group consisting of LiCl, LiBr, LiI, $K_3PO_4$, $Na_2CO_3$, $Cs_2CO_3$, $Me_2NBu^n$, pyridine, TEA (triethylamine), DIPEA (diisopropylethylamine) N-Methylpyrrolidione and N-methylpiperidine.

6. The method according to claim 3, wherein the amount of palladium catalyst is in the range of 1 to 10% by mol based on the amount of the nucleophile.

7. The method according to claim 1, wherein an additive is used in the reaction and is selected from a lithium halide (LiX, wherein X is Cl, Br, or I), an inorganic additive, or an organic amine and the amount of the additive to be used is in the range of 1.0 to 4.0 times an equivalent weight of the nucleophile.

8. The method according to claim 1, wherein a solvent is used in the reaction and is selected from the group consisting of dimethylformamide, dimethylacetamide, toluene, xylene and tetrahydrofuran and the reaction is carried out at a temperature in the range of 70 to 110 degrees Celsius.

9. The method according to claim 4, wherein the amount of phosphine ligand is in the range of 1 to 10% by mol based on the amount of the nucleophile.

* * * * *